United States Patent
Ritts

[11] Patent Number: 6,110,133
[45] Date of Patent: Aug. 29, 2000

[54] CONVERTIBLE ACROMIOCLAVICULAR STABILIZER

[75] Inventor: Graham Douglas Ritts, Duluth, Minn.

[73] Assignee: Hockey Innovations, Inc., Duluth, Minn.

[21] Appl. No.: 09/085,703

[22] Filed: May 28, 1998

Related U.S. Application Data

[60] Provisional application No. 60/048,619, Jun. 4, 1997, and provisional application No. 60/060,017, Sep. 25, 1997.

[51] Int. Cl.[7] ..................................................... A61F 5/00
[52] U.S. Cl. ........................................ 602/4; 128/DIG. 19
[58] Field of Search ............................... 602/4, 5, 19, 20; 128/875, DIG. 19; 2/44, 45

[56] References Cited

U.S. PATENT DOCUMENTS

| | | |
|---|---|---|
| 396,837 | 1/1889 | Shockey . |
| 636,562 | 11/1899 | Rouse . |
| 1,808,422 | 6/1931 | McDonald . |
| 3,404,680 | 10/1968 | Gutman et al. . |
| 4,188,944 | 2/1980 | Augustyniak . |
| 4,480,637 | 11/1984 | Florek .......................................... 602/4 |
| 4,491,129 | 1/1985 | Lockwood . |
| 4,751,923 | 6/1988 | Marino ........................................ 602/4 |
| 5,122,111 | 6/1992 | Sebastian et al. ........................ 602/19 |
| 5,181,906 | 1/1993 | Bauerfeind ................................ 602/63 |
| 5,358,470 | 10/1994 | Johnson .................................. 602/4 X |
| 5,413,552 | 5/1995 | Iwuala ......................................... 602/4 |
| 5,487,724 | 1/1996 | Schwenn . |
| 5,538,499 | 7/1996 | Schwenn et al. . |
| 5,865,166 | 2/1999 | Fitzpatrick et al. ................... 602/13 X |

*Primary Examiner*—Stephen R. Crow
*Assistant Examiner*—Denise Pothier
*Attorney, Agent, or Firm*—Dorsey & Whitney LLP

[57] ABSTRACT

The present invention provides an acromioclavicular stabilizer including a waist band, a shoulder strap, a pad carried by the strap for positioning in the location of the acromioclavicular joint and an elbow cuff removably coupled to the waist band or shoulder strap. The present invention is adapted for non-surgical or post-operative care for reducing anatomically deforming forces present in AC separations or dislocations, and is convertible from a sling and stabilizer configuration to a stabilizer only configuration.

5 Claims, 3 Drawing Sheets

CONVERTIBLE ACROMIOCLAVICULAR STABILIZER

The present application claims the priority benefit of two U.S. provisional applications, Ser. No. 60/048,619, filed Jun. 4, 1997 and Ser. No. 60/060,017, filed Sep. 25, 1997.

BACKGROUND

The present invention relates to orthopedic appliances and, more particularly, to an acromioclavicular strap-type stabilizer and supporting brace.

In orthopedics, the therapeutic value of immobilization, complete or partial, and pressure or tension has long been recognized. Orthopedic appliances have been designed for virtually every area of the human body to immobilize, provide support and/or provide tension or pressure to fractures or at dislocation sites. In some instances, an appliances may allow or provide for a degree of movement of the injured portion of the body or an adjacent limb.

One example of an orthopedic appliance is the clavicle apparatus disclosed in U.S. Pat. No. 1,808,422 (MacDonald). The disclosed apparatus is designed for maintaining the reduction of a fractured clavicle on either side of the body. It includes a half vest, vest bow, arm band, axilla pad, an elbow sling and a forearm sling. At least portions of the MacDonald clavicle apparatus are formed of elastic material, but it is not designed to provide a downwardly directed reduction force on the acromioclavicular joint. Also, to free the arm supported or confined by the slings and the arm band would be time consuming.

U.S. Pat. No. 3,404,680 (Guttman) discloses a surgical sling adapted for use on injuries around the shoulder girdle. The sling applies pressure to the collar bone where desired, is adjustable, and can be removed and replaced by the patient wearing it. The sling is made of webbing or strapping and includes a shoulder pad or collar bone engaging pad preferably made of sponge rubber, enclosed in a soft leather covering. The sling also includes an arm supporting sling feature. The ends of the sling are provided with a hook and loop material for connecting them to each other. Like the MacDonald clavicle apparatus, the Guttman sling requires an upper arm embracing loop, a strap for holding the upper arm of the user in close proximity to the body.

U.S. Pat. No. 4,491,129 (Lockwood) discloses a strapping assembly method for the treatment of acromioclavicular separations wherein the assembly includes a stocking that is worn on the leg of a patient on the side opposite the injury. This stocking serves as an anchor. A tension member is connected to the stocking through an adjustable garter and extends upwardly across the patient's back to the shoulder on the side of the injury then over the shoulder and downward to the patient's forearm. The strap is looped around the forearm to hold it in sling fashion, and the weight of the forearm places the strap under tension. While the stocking may provide an anchor, unless the forearm is constantly and completely relaxed, the variable force produced by the forearm makes it difficult to maintain fairly constant compression on the acromioclavicular separation.

U.S. Pat. Nos. 5,487,724 and 5,538,499 (Schwenne et al.) disclose orthopedic shoulder braces that are designed to evenly distribute weight onto a patient's waist and hip. The braces include generally rigid anatomically conforming shells connected by straps. While the Schwenne et al. braces may permit some movement, they include a rigid upright portion and upper arm support portions and are designed primarily for immobilization and support.

U.S. Pat. No. 4,188,944 (Augustyniak) discloses an acromioclavicular-clavicular restoration brace having a resilient and shape-retentive shoulder block having an arcuate concavity adapted to rest upon the clavicular joint of a patient, and a lower, forearm block for receiving the patient's forearm. The shoulder block is mounted on straps forming a harness which retains the block on the joint and applies a downward force on the block. The shoulder and upper body straps are made of elastic, and the upper body loop is connected to the shoulder strap. In use, the shoulder strap is placed on the patient with the shoulder block in position on the acromioclavicular-joint and the forearm resting in the lower block. A buckle is provided to adjust the vertical tension in the shoulder strap, but the carrying of the arm at the bottom of the strap may cause too much variation in the tension. While the Augustyniak patent mentions that there are drawbacks with existing devices because they excessively immobilize the entire body, and the Augustyniak brace may be less confining than some, releasing the arm from the lower block to use the arm on the injured side would cause an immediate reduction in pressure on the acromioclavicular joint possibly causing pain or reinjuring the joint or the clavicle.

It would be advantageous if there were an orthopedic appliance which could apply substantially even, constant pressure to the acromioclavicular joint, while minimizing the confinement and discomfort of a person wearing the appliance and permitting the selective use of the wearer's arm on the injured or treated side of the body without substantially disrupting the pressure on the acromioclavicular joint.

SUMMARY

The present invention provides an acromioclavicular stabilizer, and method for its use, comprising a simple strap arrangement for reducing anatomically deforming forces associated with an acromioclavicular ("AC") separation and/or dislocation. It provides substantially constant pressure to the acromioclavicular joint, while permitting the selective use of the wearer's arm on the injured or treated side of the body. The strap arrangement of the present invention provides for non-surgically restoring a dislocated or broken clavicle to its proper position. It also may be used to provide post-operative support and stabilization of the AC joint.

In one embodiment, the present invention comprises a waist band, a shoulder strap (which also may be referred to as the reduction strap), a pad and an elbow cuff sling member. The shoulder strap is coupled to the waist band. The pad is slidably carried by the shoulder strap, and the elbow cuff is removably coupled to the shoulder strap. The pad should be suitable for conforming to the AC joint and shoulder contour. When worn on the elbow of the arm on the injured or treated side, and attached to the shoulder strap, the elbow cuff supports that arm. A feature of this embodiment of the invention is the easy separability of the cuff and strap. Another feature is that the invention applies stabilizing and reducing forces to the AC joint by virtue of the elasticity of the shoulder strap, with the reduction force enhanced by the weight of the arm when the elbow cuff is in use, i.e., when the stabilizer is in its stabilizing and sling configuration.

In another embodiment, the invention provides an acromioclavicular stabilizer and method for stabilizing AC separations or dislocations including a waist band, a shoulder strap and a pad carried by the strap for positioning in the location of the acromioclavicular joint. Optional elbow and wrist cuffs may be included for selective coupling to the elbow and wrist of a patient, and for selective, removable coupling to the waist band and/or shoulder strap. The present invention is adapted for non-surgical or post-operative care for reducing anatomically deforming forces present in AC separations or dislocations, and is convertible from a sling and stabilizer configuration to a stabilizer only configuration.

An advantage of the present invention is that it provides for easy transition from an arm supporting sling configuration, wherein the elbow, and/or wrist, may be supported and substantially completely immobilized, to a sport brace configuration wherein the arm on the injured side is substantially freely usable while tension or pressure is maintained on the AC joint. Another advantage is that the stabilizer may be conveniently converted from a configuration wherein both the wrist and elbow are supported to a configuration wherein one or the other are supported.

Preferably, the stabilizer of the present invention includes hook and loop attachment means adjacent to at least one end of the shoulder strap and both ends of the waist band, and for connecting the elbow cuff around the elbow on which it is worn and to the shoulder strap. The optional wrist cuff may be attached similarly, and the pad for contacting the AC joint may be selectively positionable by being slidably received on the strap or by having a hook and loop type fabric portion complementary to the material of at least a portion of the shoulder strap.

Another advantage of the AC stabilizer of the present invention is that it is simple and comfortable and includes an easily detachable acute care elbow cuff sling feature whereby it is very convenient for a user to detach the cuff from the rest of the stabilizer for freedom of movement of the arm on the injured side. The present invention requires less hardware (buckles, straps, etc.) than known AC braces, and is designed to be less expensive and more convenient for users. These features encourage prescribed use by patients, thereby improving post-operative or post injury recovery time.

The preceding and other features and advantages of the present invention will become more fully apparent and understood with reference to the following description and drawings, and the appended claims.

DETAILED DESCRIPTION

The accompanying Figures depict embodiments of an acromioclavicular (AC) stabilizer strap in accordance with the present invention, features and components thereof, and a method of use thereof. With regard to means for fastening, mounting, attaching or connecting the components of the present invention to form the device as a whole, unless specifically described otherwise, such means are intended to encompass conventional fasteners such as hook and loop material, buttons and button holes, snap rings, such as "D-rings", snap-type devices comprising complementary members, clamps, rivets, pins and the like. Components may also be connected adhesively, by friction, sewing, or welding or deformation, if appropriate. Unless specifically otherwise disclosed or taught, materials for making components of the present invention are selected from appropriate materials such as metal, metallic alloys, elastic material, neoprene, natural or synthetic fibers, plastics and the like, and appropriate manufacturing or production methods, including casting, extruding, molding may be used.

Any references or front and back, right and left, top and bottom, upper and lower, and horizontal and vertical are intended for convenience and description, not to limit the present invention or its components to any one positional or special orientation. This is particularly true with respect to the use of the present invention on the right or left side of the patient, since it may be used equally conveniently and effectively on either acromioclavicular joint.

Figure 1:
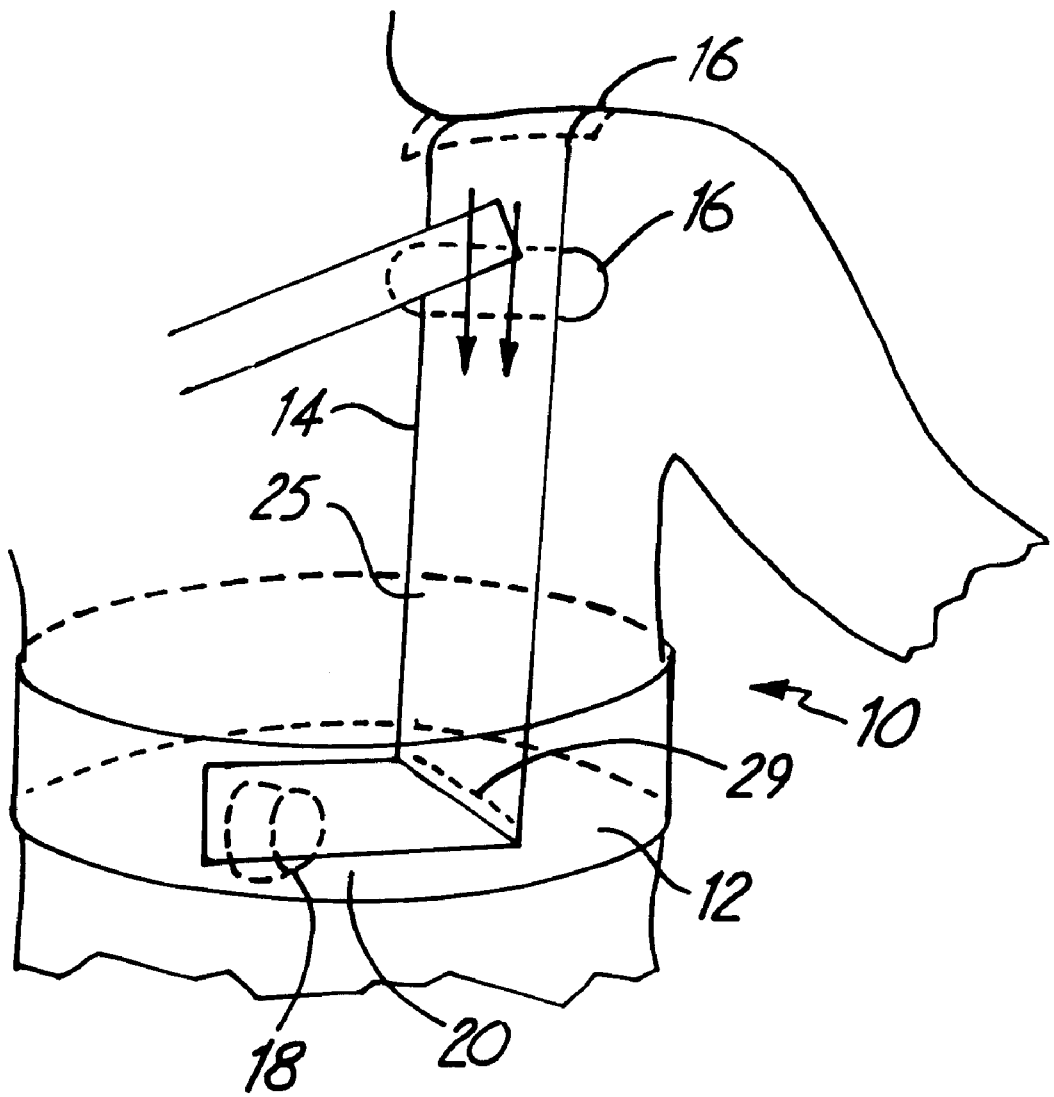
FIG. 1 is an elevational view of one embodiment of the present invention as it might be disposed in use.

Referring to the Figures, particularly FIG. 1, in one embodiment, the stabilizer 10 of the present invention comprises a belt-like, continuous waist band 12 and a continuous shoulder strap 14. The shoulder strap slidably carries a pad 16 (also shown in phantom in an alternate position generally at the top of the shoulder), and a wrist cuff 18 may be removably coupled to the waist band. Complementary hook and loop type fabric, indicated for example at 20, or the like may be used to connect the ends of the waist band 12, and to connect the shoulder strap 14 to the waist band 12. As depicted, the waist band 12 is adapted to fit securely around the waist generally under the rib cage, and preferably may be formed by an elasticized material with a textured inside surface to preclude slippage. In use, the shoulder strap 14, which may be approximately 26 inches long and 3 inches wide, exerts a downward pressure (shown at arrows "p") against the top of the shoulder in the vicinity of the AC joint or the free end of the clavicle "C" to reduce an acromioclavicular separation. The wrist cuff 18 is worn on the wrist and removably connected to the waist band 12 to provide for support in acute injuries where the arm on the injured side needs to be supported, and to permit freedom of movement of the arm in less severe injuries, in which case the removable wrist cuff 18 can be disconnected from the waist band 12.

Figure 2:
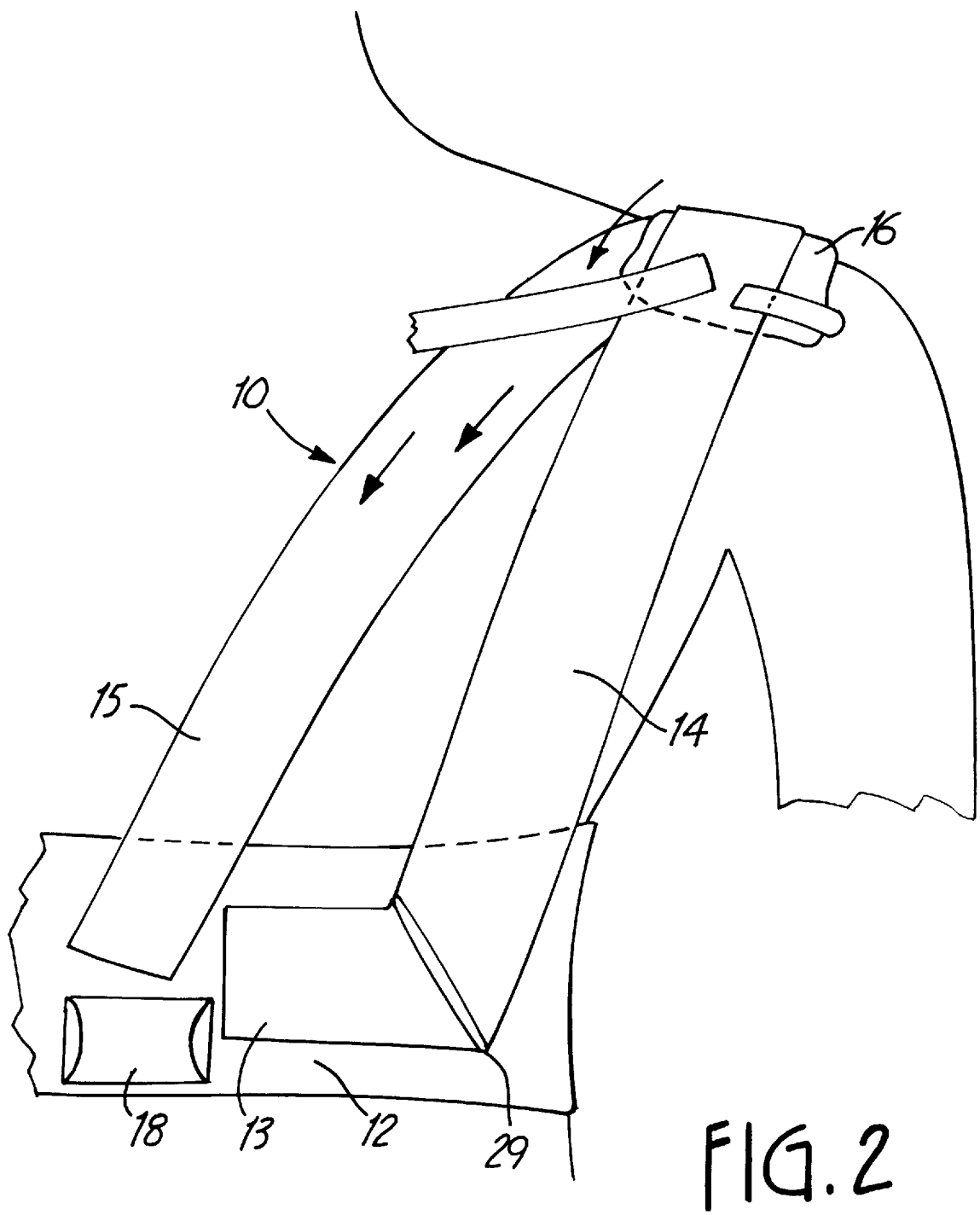
FIG. 2 is a view similar to that of FIG. 1 depicting another embodiment of the present invention.

Referring to FIG. 2, the pad 16, which may be formed of suitable cushioning, resilient material or which may comprise an air filled or partially air filled cell, is carried approximately midway between the ends of the shoulder strap 14 for positioning over the acromioclavicular joint. Any size pad 16 may be provided as long as user comfort and therapy are not jeopardized. Note that one end of the shoulder strap 14, typically the rear or anterior end 15, may be permanently or semi-permanently connected to the waist band 12. The anterior or front end 13 of the shoulder strap 14 could also be permanently or semi-permanently connected to the waist band 12, but for ease of use, it is preferable that the front end 13 of the shoulder strap 14 is free until coupled to the waist band 12. A suitable coupler is a combination of a D-ring type connector 29 and a hook and loop fabric portion near or at the free end 13 of the shoulder strap 14.

Figure 3:
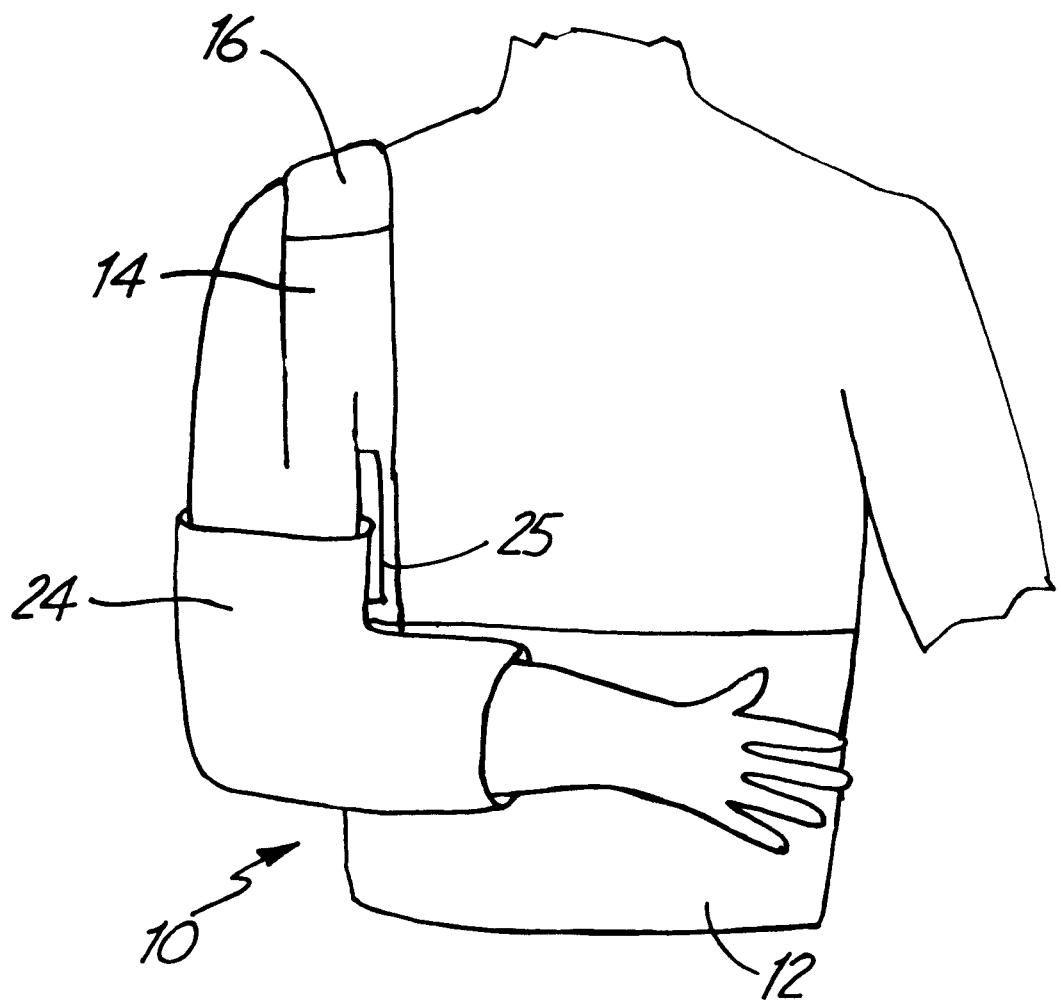
FIG. 3 depicts another embodiment of the present invention wherein an elbow cuff is provided.

FIG. 3 depicts an embodiment of the stabilizer 10 of the present invention wherein an elbow cuff 24 is incorporated. The elbow cuff 24 may be formed of material similar to the material of the wrist cuff 18, and is designed to closely wrap and support the wearer's elbow and arm. The elbow cuff 24 preferably includes one of a hook or loop type fabric region or is interactive with hook and loop type fabric whereby it can be removably coupled to a hook and loop region 25 of the shoulder strap 14. The elbow cuff 24 may be used in conjunction with the wrist cuff 18, or either may be used alone.

In use, a patient puts on the waist band 12 and secures it around the waist using hook and loop type connectors and/or connecting and force directing means, for example, the D-ring like buckle member depicted in FIGS. 1 and 2. The D-ring arrangement is advantageous because it helps dissipate upward force on the waist band 12, reducing any tendency for the waist band to move upwardly. At this point, the shoulder strap 14 is hanging behind the patient's back. The free end 13 of the shoulder strap 14 may then be brought upwardly and over the injured or treated shoulder with the air cell pad 16 approximately in place over the AC joint, and may be connected to the waist band 12 or doubled back and connected to the shoulder strap 14 (not shown). The amount of force applied to the AC joint may be adjusted by how far the shoulder strap 14 is tightened before being secured to the waist band 12. The AC joint pad 16 may be slid along the shoulder strap 14 until comfort and/or optimum reduction is achieved. The removable elbow cuff sling member 24 may be coupled to the shoulder strap 14, to provide support for acute injuries, for a period of time, or intermittently for periodic support.

An advantage of the present invention is that it may be used with the optional wrist and elbow cuff sling members attached to the shoulder strap 14 or to the waist band 12, as shown in FIGS. 1–3. Another advantage is that, since the cuffs are coupled using hook and loop fabric or the like, they can be quickly and easily detached to convert the stabilizer 10 from its arm supporting sling configuration to a tensioning only configuration for providing reducing tension to the acromioclavicular joint while the arm on the injured side is substantially free of restraint. In the latter configuration, the cuffs, or cuff, may be retained on the patient's elbow and/or wrist for convenient reattachment to the shoulder strap 14.

In one embodiment, the strap material for forming all or portions of the straps of the present invention comprise a latex inner surface layered with a fabric. The shoulder strap 14 may be provided in selected lengths and widths, and the material for the shoulder strap 14 may be selected to provide for adjustable tension on the AC joint. Adjustability may be enhanced by using or incorporating a buckle and/or slide arrangement with the shoulder strap 14. The material for forming the straps can be elasticized along the entire length of the straps or for a portion thereof. One or more pads 16 may be used with the stabilizer 10, and the pad or pads 16 may be integrated with the shoulder strap 14, by providing a thickened, padded region of the strap 14, or the strap may include one or more inflatable or self-inflatable air cells or bladders.

The present invention may be embodied in other specific forms without departing from the essential spirit or attributes thereof. It is desired that embodiments described herein be considered in all respects as illustrative not restrictive, and that reference be made to the appended claims for determining the scope of the invention.

What is claimed is:

1. A stabilizer for reducing separation of a wearer's acromioclavicular joint, comprising:

a band sized to fit around the wearer's torso below the wearer's shoulder region;

a reducing strap coupled with the band and sized to pass over the top of the wearer's shoulder region in the vicinity of the acromioclavicular joint, the ends of said reducing strap coupled to said band permanently at one end and releaseably at the other end, said reducing strap having a first portion and a second portion, wherein, when in use, the second portion of said reducing strap extends substantially along a line of path of said band around the wearer's torso and releaseably couples said reducing strap band to dissipate upward force on said band;

a pad coupled to the reducing strap for conforming to and engaging the body of the wearer in the vicinity of the acromioclavicular joint, wherein the reducing strap and the pad are adapted to apply a dislocation reducing pressure to the wearer's acromioclavicular joint; and an elbow cuff removably coupled directly to the reducing strap for releasably supporting the wearer's arm, wherein, when in use, the elbow cuff and reducing strap are on one side of the wearer's body and a line defined by the first portion of the reducing strap positioned along the front of the wearer's body intersects with the elbow cuff, and wherein the elbow cuff uses the weight of the weaer's arm to augment the dislocation reducing pressure applied to the acromioclavicular joint of the wearer when in use.

2. The stabilizer according to claim 1, wherein the reducing strap and the pad are adapted to apply the dislocation reducing pressure in the downward and anterior direction to stabilize the acromioclavicular joint.

3. The stabilizer according to claim 1, wherein the pad is slidably attached to the reducing strap so that the location of the pad relative to the reducing strap can be adjusted.

4. The stabilizer according to claim 1, wherein the pad is an air filled cell.

5. The stabilizer according to claim 4, wherein the volume of the air filled cell may be adjusted.

* * * * *